US009877892B2

(12) United States Patent
Grant et al.

(10) Patent No.: US 9,877,892 B2
(45) Date of Patent: Jan. 30, 2018

(54) SYSTEM AND METHOD FOR TITRATING IN VIVO CELLULAR REACTION AND GENE EXPRESSION USING VARYING OSCILLATION FREQUENCIES

(71) Applicant: STRATHSPEY CROWN HOLDINGS, LLC, Newport Beach, CA (US)

(72) Inventors: Robert Edward Grant, Laguna Beach, CA (US); Todd Mirzai, Honolulu, HI (US); Matthew T. Case, Laguna Hills, CA (US)

(73) Assignee: Strathspey Crown Holdings, LLC, Newport Beach, CA (US)

( * ) Notice: Subject to any disclaimer, the term of this patent is extended or adjusted under 35 U.S.C. 154(b) by 411 days.

(21) Appl. No.: 14/738,518

(22) Filed: Jun. 12, 2015

(65) Prior Publication Data

US 2016/0074277 A1 Mar. 17, 2016

Related U.S. Application Data

(63) Continuation-in-part of application No. 14/488,101, filed on Sep. 16, 2014, now abandoned.

(51) Int. Cl.
*A61B 5/055* (2006.01)
*A61H 23/02* (2006.01)

(52) U.S. Cl.
CPC . *A61H 23/0236* (2013.01); *A61H 2201/1623* (2013.01); *A61H 2201/5097* (2013.01); *A61H 2203/0456* (2013.01); *A61H 2205/081* (2013.01)

(58) Field of Classification Search
CPC ........ A61H 23/0236; A61H 2201/1623; A61H 2201/5097; A61H 2203/0456; A61H 2205/081
See application file for complete search history.

(56) References Cited

U.S. PATENT DOCUMENTS

| | | | |
|---|---|---|---|
| 6,024,690 | A | 2/2000 | Lee et al. |
| 6,033,357 | A | 3/2000 | Ciezki et al. |
| 6,077,213 | A | 6/2000 | Ciezki et al. |
| 6,221,094 | B1 | 4/2001 | Bare |
| 6,309,339 | B1 | 10/2001 | Ciezki et al. |
| 6,626,816 | B1 | 9/2003 | Ciezki et al. |
| 6,725,081 | B2 | 4/2004 | Ciezki et al. |
| 7,280,874 | B2 | 10/2007 | Boehm |
| 7,418,294 | B2 | 8/2008 | May |
| 7,500,956 | B1 | 3/2009 | Wilk |
| 8,326,408 | B2 | 12/2012 | Green et al. |
| 8,440,154 | B2 | 5/2013 | Fahs, II et al. |
| 8,591,419 | B2 | 11/2013 | Tyler |

(Continued)

*Primary Examiner* — Glenn Richman
(74) *Attorney, Agent, or Firm* — Fish IP Law, LLP

(57) ABSTRACT

A system and method for directing vibrational oscillating sonic waves toward a target tissue in the body of a person, to thereby influence a phenotypic differentiation of the target tissue at a cellular level, requires the use of an epidermal or implantable patch. Mounted on the patch is a sonic generator for generating sonic energy that entrains cellular functions of the target tissue for a desired phenotypic response. Also included is a unit for titrating the target tissue to monitor for changes in an expression level of the target tissue resulting from phenotypic differentiation.

20 Claims, 1 Drawing Sheet

(56) References Cited

U.S. PATENT DOCUMENTS

| | | | | |
|---|---|---|---|---|
| 8,845,629 | B2 * | 9/2014 | Demarais ................. | A61N 7/02<br>601/1 |
| 2010/0222723 | A1 * | 9/2010 | Hoffmann ................ | A61B 8/08<br>601/107 |
| 2015/0209564 | A1 * | 7/2015 | Lewin ...................... | A61N 7/00<br>601/2 |
| 2016/0184348 | A1 * | 6/2016 | Taneike ................... | A61K 8/19<br>601/2 |

* cited by examiner

SYSTEM AND METHOD FOR TITRATING IN VIVO CELLULAR REACTION AND GENE EXPRESSION USING VARYING OSCILLATION FREQUENCIES

This application is a continuation-in-part of application Ser. No. 14/488,101 filed Sep. 16, 2014, which is currently pending. The contents of application Ser. No. 14/488,101 are incorporated herein by reference.

FIELD OF THE INVENTION

The present invention pertains generally to systems and methods which are used for conducting sonic radiation therapy. More particularly, the present invention pertains to epidermal and/or implantable patches that generate and radiate sonic energy toward target tissue inside the body of a person for therapeutic purposes. The present invention is particularly, but not exclusively, useful for incorporation into systems and methods that are used for sonic radiation therapy and that include a titration capability for monitoring in vivo cellular and gene expression responses to the sonic radiation.

BACKGROUND OF THE INVENTION

It is well known that human beings will physically react to sonic energy. Hearing is but one example of this phenomenon. It often happens, however, that the human reaction to sonic energy is not immediately perceptible. Instead, the perception is the result of a longer term evolutionary process. In this last category, in vivo cellular reactions and gene expressions have been attributed to the influence of sonic radiation. Of particular interest here are cellular reactions that result in a phenotypic differentiation of the target tissue.

Apart from the phenotypic cell differentiation that can result from exposure to sonic radiation, it is also known that meditative states and/or alpha brain wave/relaxation states are greatly influenced by sonic radiation. On this point, consider the effect music can have on an individual. Also, consider the effect an exposure to loud, abrasive and/or startling noises can have on an individual, regardless whether the sound is instantaneous, repetitive or continuous.

Although a wide variety of protocols for sonic radiation therapy have been, and can be, proposed, it is axiomatic that for beneficial therapy, sonic radiation must be effectively directed onto the proper target tissue. With this objective in mind, an effective delivery of sonic radiation necessarily requires a controlled exposure to the radiation. This control, in turn, requires the employment of preplanned operational parameters for the radiation (i.e. frequency, intensity, and duration), at predetermined exposure intervals. Preferably, all this is done with minimal requirements for patient supervision.

With the above in mind, it is an object of the present invention to provide a system and method for directing vibrational oscillating sonic waves toward a target tissue in the body of a person to influence a phenotypic differentiation of the target tissue at a cellular level. Another object of the present invention is to provide a system and method for using sonic radiation to induce meditative states and/or to establish alpha brain wave/relaxation states for the user. Yet another object of the present invention is to provide a system and method for monitoring the efficacy of sonic radiation therapy by employing a titration capability in the operational protocol. Still another object of the present invention is to provide a system and method for providing sonic radiation therapy that is easy to use, is simple to implement, and is relatively cost effective.

SUMMARY OF THE INVENTION

In accordance with the present invention a system is provided for directing sonic waves toward preselected target tissue within the body of a person. This can be done for any of several reasons. For one, the sonic waves can be directed toward tissue to improve the overall health and wellness of the person. For another, they can be used to induce meditative states and/or to establish alpha brain wave/relaxation states for the person.

As envisioned for the present invention, the system will include a patch that is somehow attached to the human body. Thus, it may be either an epidermal patch or an implantable patch. In either case, and regardless where it is positioned on the user, the overall functionality of the patch is to direct sonic waves toward target tissue of the user in a manner that will entrain cellular functions locally in the target tissue, for an intended purpose.

Structurally, for a monopolar version of a system for the present invention, the patch will include a base member and a sonic generator which is mounted on the base member. In the case of an epidermal patch, a connector is also included which may be either a fastener or an adhesive. For its use, the connector is affixed to the base member to hold the patch at a preselected location (position) on the body of the person (user).

Typically, a sounding board (speaker cone) is employed with the sonic generator on the base member of the patch. If used, the sounding board (speaker cone) will concentrate and more accurately direct operationally effective sonic frequencies toward the target tissue. Further, a transceiver can be mounted on the base member of the patch to establish a communication link between the sonic generator and a remote central control unit. In particular, the information to be transmitted by the transceiver from the patch to the central control unit will typically pertain to information that is pertinent to the operation of the sonic generator.

An extracorporeal titration unit is incorporated into the present invention to provide for communication between the patch and the central control unit. Specifically, the titration unit is employed to monitor the influence that the sonic waves have on the target tissue. In detail, the titration unit monitors changes of an expression level of the target tissue that result due to phenotypic differentiation of the tissue's cellular structure. This monitoring by the titration unit can be accomplished in either of several ways. For example, it can be accomplished using any of various imaging technologies, such as Optical Coherence Tomography (OCT) and ultrasound. The monitoring can also be accomplished by periodically conducting biopsies of the target tissue, or by taking periodic bio-impedance measurements.

For a bipolar version of the present invention, a second patch can also be employed in combination with the monopolar patch disclosed above. Like the patch for the monopolar embodiment disclosed above, this second patch may be either an epidermal or an implantable patch. Similarly, it can also be used anywhere on the body of the user. When used, the second patch will typically be complementary to the operation of the other patch. For instance, the second patch can be positioned on the opposite side of the body from the first patch to enhance bio-impedance measurements. It can also be used to radiate sonic energy simultaneously with the first patch to achieve different radiation perspectives on the target tissue.

Operationally, the system of the present invention can be employed to generate sonic waves in accordance with a scheduled program. As envisioned for the present invention, this program can provide for variations in the intensity and/or magnitude of oscillating frequencies of the sonic wave. Preferably, each frequency that is to be used will be selected from a sonic spectrum that includes ultrasonic, audible sonic, and infrasonic frequencies.

As implied above, the functionality of the present invention is established to achieve an intended outcome for the target tissue. In particular, this outcome will most likely be a phenotypic response for the target tissue. To achieve this, the titration unit monitors the target tissue during employment of the patch (system). Signals that are pertinent to the expression level (phenotypic differentiation) of the target tissue are then sent from the monitor to the central control unit. At the central control unit they are methodically compared with a desired phenotype (i.e. a base reference). Based on this comparison, employment of the system may be either continued or terminated. In particular, a use of the system for the present invention is to be terminated whenever the desired phenotype response has been achieved.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
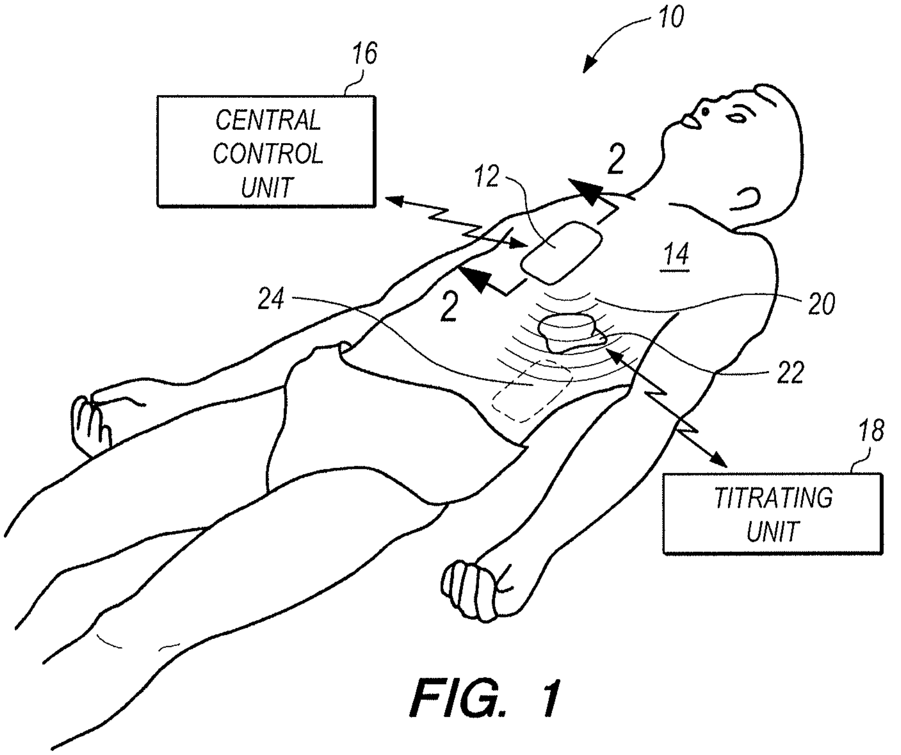
FIG. 1 is a perspective view of an epidermal patch in accordance with the present invention, shown in location on the body of a user, together with associated system operating components.

Referring initially to FIG. 1 a system for titrating in vivo cellular and gene expression therapies using varying oscillation frequencies is shown, and is generally designated 10. As shown, the system 10 includes a patch 12 that is somehow mounted on the body of a patient/user 14. For purposes of the present invention, the patch 12 may be either epidermal or implantable. FIG. 1 also shows that the system 10 includes a central control unit 16 and a titrating unit 18. As envisioned for the present invention, the central control unit 16 will typically be extracorporeal and will be connected in a wireless communication with the patch 12. As also envisioned for the present invention, the titrating unit 18 will be extracorporeal and can be any type of monitoring unit known in the pertinent art that is capable of accomplishing the intended purpose(s) of the present invention, such as an Optical Coherence Tomography (OCT) unit or an ultrasound unit.

Still referring to FIG. 1, it will be appreciated that the intended purpose for the patch 12 is to direct sonic radiation 20 onto target tissue 22 inside the body of the patient/user 14. FIG. 1 also shows that for a bipolar embodiment of the present invention, a second patch 24 can be incorporated into the system 10. In general, the second patch 24 will be substantially the same as patch 12. Accordingly, the disclosure below pertains to patch 24 as well as patch 12.

Figure 2:
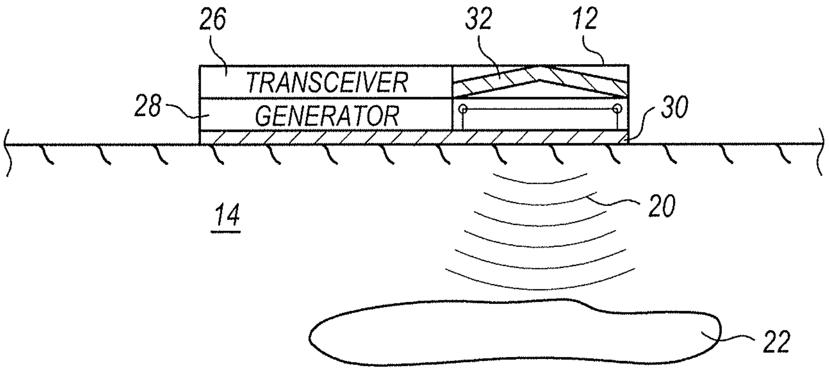
FIG. 2 is a cross-section view of the epidermal patch as seen along the line 2-2 in FIG. 1.

In FIG. 2 it will be seen that the patch 12 itself includes a transceiver 26, a generator 28, an adhesive 30 and a sounding board (speaker cone) 32. In this combination, the transceiver 26 is provided to establish communication with the central control unit 16; the generator 28 is provided to give transmitting power to the sounding board (speaker cone) 32; and the adhesive 30 is provided as a means for attaching the patch 12/24 to the body of the patient/user 14.

For an operation of the present invention, a protocol is selected for the particular purpose of the intended operation of system 10. Essentially, this requires establishing operational parameters for the sonic radiation 20. In detail, the selection of a frequency or frequencies, the intensity of each frequency to be used, the establishment of timed radiation intervals, the type of radiation to be employed (i.e. pulsed or continuous), and time requirements for the protocol are all to be considered as operational parameters. Furthermore, possible variations in any of these parameters during the course of a protocol are also to be considered.

As envisioned for the present invention, a selected protocol can be entered or pre-programmed in the central control unit 16. The protocol is then transmitted to the transceiver 26 of the patch 12/24, and the generator 28 is activated to operate the sounding board (speaker cone) 32 for directing sonic radiation 20 onto the target tissue 22.

It is also envisioned by the present invention that during the conduct of a protocol, the titrating unit 18 will be employed to monitor a phenotypic differentiation of the target tissue 22 at the cellular level. As disclosed above, this monitoring can be accomplished using OCT and/or ultrasound techniques. Additionally, it may be desirable to evaluate the target tissue 22 by periodically taking a biopsy of the target tissue 22.

An alternative protocol that may either complement phenotypic cell differentiation, or be conducted separately, is also envisioned for the present invention. In this case, the operational parameters set forth above can be selected to induce meditative states and/or to establish alpha brain wave/relaxation states for the patient/user 14. In all instances, regardless whether system 10 is used with a monopolar configuration (i.e. patch 12 only) or a bipolar configuration (i.e. both patch 12 and patch 24) the particular protocol to be followed is dependent on the needs of the patient/user 14.

While the particular System and Method for Titrating In Vivo Cellular Reaction and Gene Expression Using Varying Oscillation Frequencies as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system is provided for directing vibrational oscillating sonic waves toward a target tissue in the body of a person to influence a phenotypic differentiation of the target tissue at a cellular level, the system comprising:

a patch having a base member;

a means for holding the base member in a preselected location on the person;

a sonic generator mounted on the base member for generating a sonic wave in accordance with a scheduled program, wherein the sonic wave includes at least one predetermined frequency from the program to entrain cellular functions of the target tissue for a desired phenotypic response; and a unit for titrating the target tissue to monitor for changes in an expression level of the target tissue resulting from phenotypic differentiation, and to indicate a termination of epidermal patch operation when the desired phenotypic response has been achieved.

2. The system as recited in claim 1 further comprising a sounding board mounted on the base member to direct vibrational oscillation frequencies of the sound wave toward the target tissue, wherein the means for holding the base member on the person is a connector selected from a group consisting of a fastener and an adhesive.

3. The system as recited in claim 1 further comprising:

a transceiver mounted on the base member and connected with the sonic generator; and a central control unit for receiving signals from the transceiver, wherein the signals include information pertinent to the operation of the sonic generator.

4. The system as recited in claim 3 wherein the titration unit is connected to the central control unit to provide the central control unit with epigenetic information regarding the expression level of the target tissue pertinent to the phenotypic differentiation of the target tissue.

5. The system as recited in claim 4 wherein the central control unit varies the frequency of the sonic wave in accordance with the scheduled program, and compares information from the titration unit with the desired phenotypic response to determine when the desired phenotypic response has been achieved.

6. The system as recited in claim 4 wherein the titration unit is selected from a group consisting of an Optical Coherence Tomography (OCT) device, and an Ultrasound device.

7. The system as recited in claim 4 wherein the titration unit requires a biopsy of the target tissue.

8. The system as recited in claim 1 wherein the predetermined sonic frequency is selected from a sonic spectrum including infrasonic, audible sonic, and ultrasonic frequencies, and further wherein the phenotypic response is selected from the group consisting of improved health and wellness, and meditative and brain wave/relaxation states.

9. The system as recited in claim 1 wherein the sonic wave has a frequency resonant with the natural frequency of the target tissue.

10. The system as recited in claim 1 wherein the patch in implantable.

11. A method for directing vibrational oscillating sonic waves toward a target tissue in the body of a person to influence a phenotypic differentiation of the target tissue at a cellular level, the method comprising the steps of:

positioning a patch having a base member at a preselected location on the person, wherein the patch includes a sonic generator;

operating the sonic generator to generate a sonic wave in accordance with a scheduled program, wherein the sonic wave includes at least one predetermined frequency from the program to entrain cellular functions of the target tissue for a desired phenotypic response; and titrating the target tissue to monitor for changes in an expression level of the target tissue resulting from phenotypic differentiation, and to indicate a termination of epidermal patch operation when the desired phenotypic response has been achieved.

12. The method as recited in 11 further comprising the step of sending signals from the patch to a central control unit, wherein the signals include information pertinent to the operation of the sonic generator.

13. The method as recited in claim 12 further comprising the step of comparing the monitored information resulting from phenotypic differentiation with the desired phenotypic response to determine when the desired phenotypic response has been achieved.

14. The method as recited in claim 13 wherein the information resulting from phenotypic differentiation is epigenetic information regarding the expression level of the target tissue.

15. The method as recited in claim 14 further comprising the step of varying the frequency of the sonic wave in accordance with the scheduled program.

16. The method as recited in claim 11 wherein the titrating step is accomplished using a device selected from a group consisting of an Optical Coherence Tomography (OCT) device, an ultrasound device and instruments for performing a biopsy of the target tissue.

17. The method as recited in claim 11 wherein the predetermined sonic frequency is selected from a sonic spectrum including infrasonic, audible sonic, and ultrasonic frequencies, and further wherein the phenotypic response is selected from the group consisting of improved health and wellness, and meditative and brain wave/relaxation states.

18. The method as recited in claim 11 wherein the sonic wave has a frequency resonant with the natural frequency of the target tissue.

19. An epidermal patch for directing vibrational oscillating sonic waves toward a target tissue in the body of a person to influence a phenotypic differentiation of the target tissue at a cellular level which comprises:

a base member;

a means for holding the base member in a preselected location on the person;

a sonic generator mounted on the base member for generating a sonic wave in accordance with a scheduled program, wherein the sonic wave includes at least one predetermined frequency from the program to entrain cellular functions of the target tissue for a desired phenotypic response;

a unit for titrating the target tissue to monitor for changes in an expression level of the target tissue resulting from phenotypic differentiation, and to indicate a termination of epidermal patch operation when the desired phenotypic response has been achieved;

a transceiver mounted on the base member and connected with the sonic generator; and a central control unit for receiving signals from the transceiver, wherein the signals include information pertinent to the operation of the sonic generator.

20. The patch as recited in claim 19 wherein the titration unit is connected to the central control unit to provide the central control unit with epigenetic information regarding the expression level of the target tissue pertinent to the phenotypic differentiation of the target tissue, and wherein the central control unit varies the frequency of the sonic wave in accordance with the scheduled program, and compares information from the titration unit with the desired phenotypic response to determine when the desired phenotypic response has been achieved.

* * * * *